(12) United States Patent
Nakano

(10) Patent No.: US 9,431,224 B2
(45) Date of Patent: Aug. 30, 2016

(54) CHROMATOGRAPH MASS SPECTROMETER

(75) Inventor: Shigenobu Nakano, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 13/090,120

(22) Filed: Apr. 19, 2011

(65) Prior Publication Data

US 2011/0303842 A1 Dec. 15, 2011

(30) Foreign Application Priority Data

Jun. 14, 2010 (JP) ................... 2010-135422

(51) Int. Cl.
*H01J 49/26* (2006.01)
*H01J 49/00* (2006.01)
*G01N 30/72* (2006.01)

(52) U.S. Cl.
CPC ............. *H01J 49/004* (2013.01); *G01N 30/72* (2013.01); *H01J 49/0027* (2013.01)

(58) Field of Classification Search
CPC ... G01N 30/72; H01J 49/004; H01J 49/0027
USPC ........................................ 250/281, 282, 288
See application file for complete search history.

(56) References Cited

U.S. PATENT DOCUMENTS

| 7,558,682 B2 * | 7/2009 | Yamamoto | H01J 49/0036 702/23 |
| 2004/0108452 A1 * | 6/2004 | Graber | G01N 33/6803 250/281 |

(Continued)

FOREIGN PATENT DOCUMENTS

| JP | 2008-298427 | 12/2008 |
| JP | 2008-298427 A | 12/2008 |

(Continued)

OTHER PUBLICATIONS

Zhang, Y., et al., "Effect of Dynamic Exclusion Duration on Spectral Count Based Quantitative Proteomics" Anal. Chem. 2009, 81, 6317-6326.*

(Continued)

*Primary Examiner* — Wyatt Stoffa
(74) *Attorney, Agent, or Firm* — Morgan, Lewis & Bockius LLP

(57) ABSTRACT

When performing an automatic $MS^2$ analysis on a specimen containing components that include elements whose abundance ratio of stable isotopes is close, to prevent the same component that includes isotopes of differing masses to be successively selected as a precursor ion and allow the $MS^2$ analysis of various components whose retention time to elution is close. As precursor selection conditions, the user is allowed to set in advance the time period for automatic exclusion and a m/z range (-p, q) with respect to any m/z. When the analysis is performed, a precursor selection unit selects a precursor according to a predetermined selection condition for the MS spectrum that was obtained and repeats the $MS^2$ analysis on the precursor ion (m/z=M) for the number of times that is set. Thereafter, for a specified automatic exclusion period, ions falling in a m/z range of M-p to M+q are excluded from selection as a precursor. Since ions that are derived from a component whose difference from the original component from which the ion whose m/z=M is derived is the isotopes will fall in the excluded m/z range, such ions are not used as a precursor ion.

10 Claims, 5 Drawing Sheets

(56) References Cited

U.S. PATENT DOCUMENTS

| | | | | |
|---|---|---|---|---|
| 2004/0169138 A1* | 9/2004 | Ootake | ............... | H01J 49/0036 250/281 |
| 2004/0251409 A1* | 12/2004 | Le Blanc | ............ | H01J 49/0045 250/288 |
| 2006/0118489 A1* | 6/2006 | Castro-Perez | ..... | G01N 30/8675 210/656 |
| 2006/0284069 A1* | 12/2006 | Le Blanc | ............ | H01J 49/0036 250/282 |
| 2006/0289735 A1* | 12/2006 | Ohtake | ................... | H01J 49/02 250/282 |
| 2009/0159793 A1* | 6/2009 | Hanas | ..................... | G06F 19/18 250/282 |
| 2009/0189063 A1* | 7/2009 | Sano | ................. | G01N 33/6848 250/281 |
| 2010/0133428 A1* | 6/2010 | Matsui | ............... | H01J 49/0045 250/281 |
| 2010/0286927 A1* | 11/2010 | Horn | ................... | H01J 49/0036 702/19 |
| 2011/0212847 A1* | 9/2011 | Vrana | ................. | C12Q 1/6883 506/7 |
| 2011/0243977 A1* | 10/2011 | Olmsted | ................ | A61K 39/09 424/190.1 |
| 2011/0297823 A1* | 12/2011 | Coon | .................... | H01J 49/004 250/282 |
| 2013/0228678 A1* | 9/2013 | Savitski | ............. | H01J 49/0045 250/282 |

FOREIGN PATENT DOCUMENTS

| | | |
|---|---|---|
| WO | 2009095957 A1 | 8/2009 |
| WO | WO 2009/095957 A1 | 8/2009 |

OTHER PUBLICATIONS

"Liquid Chromatograph Mass Spectrometer LCMS-IT-TOF Automatic $MS^n$ Function", Shimadzu Corporation.

Japanese Office Action mailed May 16, 2013 for corresponding Japanese Patent App. No. 2010-135422.

English translation of "Reason for Rejection" in Japanese Office Action mailed May 16, 2013 for corresponding Japanese Patent App. No. 2010-135422.

\* cited by examiner

*FIG.2*

| PRECURSOR SELECTION CONDITION SETTINGS |
|---|

SIGNAL STRENGTH LOWER LIMIT VALUE: 200

MINIMUM REPETITION COUNT: 5

☑ AUTOMATIC EXCLUSION

AUTOMATIC EXCLUSION PERIOD: 600 sec

EXCLUDED M/Z RANGE: -10 - 25 u

CHROMATOGRAPH MASS SPECTROMETER

TECHNICAL FIELD

The present invention relates to a chromatograph-mass spectrometer that uses a mass spectrometer capable of performing $MS^2$ analysis as a gas chromatograph (GC) or a liquid chromatograph (LC) detector.

BACKGROUND TECHNOLOGY

With triple quadrupole mass spectrometers (TQMS) and ion trap time-of-flight mass spectrometers (IT-TOFMS), an ion having a specific mass/charge ratio (m/z) is selected as a precursor ion from among various ions that are derived from the component being analyzed. The precursor ion is dissociated by collision induced dissociation (CID), and the product ions that are generated are subjected to mass spectroscopy to produce a MS/MS (=$MS^2$) spectrum.

With a chromatograph-mass spectrometer that combines a mass spectrometer that is capable of performing liquid chromatography, gas chromatography and $MS^2$ analysis, if the components that are present in a specimen are known, the $MS^2$ spectrum of the target compound can be obtained by setting in advance as the analysis condition the mass/charge ratio of the precursor ion that is the subject of the $MS^2$ analysis during the retention time of the component. However, if the components that are present in a specimen are unknown, it is not possible to set the mass/charge ratio of the precursor ion in advance, and it is not possible to obtain the results of the $MS^2$ analysis of the unknown components that are present in the specimen in addition to the target component. Different from this, also known in the art are mass spectrometers that are equipped with a function ("automatic $MS^2$" hereinafter) that automatically selects an appropriate precursor ion in real time and performs a $MS^2$ analysis based on the results of an MS analysis that does not use CID.

For example, Patent Literature 1 describes performing a $MS^2$ analysis by sequentially selecting a peak starting with the one with the highest signal strength among the plurality of peaks that appear in a MS spectrum generated by a MS analysis and performing $MS^2$ analysis by automatically selecting as the precursor ion the ion species that correspond to the respective peaks. The same literature also describes performing $MS^2$ analysis by selecting peaks whose signal strength fall within a predetermined strength range and automatically setting the corresponding ion species as the precursor ions. Furthermore, Patent Literature 2 and Non-Patent Literature 2 describe performing $MS^2$ analysis that entails not just setting up a sequence based on signal strength or mass/charge ratio of the plurality of peaks that appear in a MS spectrum that is obtained from MS analyses but also using such factors as valence and mono-isotonic peaks to eliminate or preferentially select ions with specific mass and charge for the automatic selection of the precursor ions which are used for an $MS^2$ analysis.

An overview of an automatic $MS^2$ function in a usual chromatograph-mass spectrometer is described next with reference to FIG. 5. Here, one peak with the highest signal strength is selected as the only precursor ion from among the peaks having a signal strength higher than a threshold value th in the MS spectrum. However, an excluded ion list and a preferential ion list are separately provided, and ions with a mass/charge ratio that is registered in the excluded ions list are not selected as a precursor ion even if the afore-described criteria is met. Conversely, ions with a mass/charge ratio that is registered in the preferential ions list are selected as a precursor ion so long as there is a peak even if the afore-described criteria is not met. Ordinarily, the excluded ions list is used so that impurity components or interfering components that are known to be present in a specimen and components that are known in advance to not require an analysis are not selected as precursor ions. Conversely, the preferential ions list are used so that components that are of interest for analysis are selected as a precursor ion even if they may be present only in minute quantities. The number of precursor ions that can be selected for any one MS spectrum is limited since there is a constraint on the amount of time available for performing a $MS^2$ analysis in real time.

Assume that a total ion current (total ion) chromatogram produces the waveform shown in FIG. 5(a) and that the MS spectrum identified as A is obtained at time t1. Based on the afore-described criteria regarding signal strength, peak f can be selected as a candidate as a precursor ion based on the MS spectrum. However, if the mass/charge ratio corresponding to peak f is registered in the excluded ions list, the ion corresponding to peak f is not selected as a precursor ion. On the other hand, even though the signal strength of peak g falls short of the threshold th, if the corresponding mass/charge ratio is registered in the preferential ions list, the ion corresponding to peak g is selected as a precursor ion, and an $MS^2$ analysis on this precursor ion is started immediately (following the MS analysis). The $MS^2$ spectrum that is obtained is identified as B.

Assume that the MS spectrum identified as C is obtained at a different time, time t2. This MS spectrum has five peaks whose signal strength exceeds the threshold th. Peaks are then selected in order starting with the peak with the highest strength. Assume that the mass/charge ratios corresponding to peaks b and d are registered on the excluded ions list. These peaks are then excluded, and the ion corresponding to the peak with the next highest strength, peak a, is selected as the precursor ion, and a $MS^2$ analysis is immediately executed on the precursor ion. The result is the $MS^2$ spectrum identified as D. With an analysis that uses the automatic $MS^2$ function, an ordinary MS analysis which does not involve a CID is repeated, and if the results of the analyses show the presence of an ion that meets the precursor selection condition, the ion is used as a precursor ion, and the $MS^2$ analysis is performed in real time.

The following problems occur with the analytic use of a chromatograph-mass spectrometer with an automatic $MS^2$ function such as the afore-described. If the specimen being analyzed includes many components whose retention time is close to each other, the number of ions that are selected as precursor ion candidates becomes numerous near that retention time. If a $MS^2$ analysis is performed while repeatedly selecting as the precursor ion only the ions that are derived from the same component, it is possible for important components to elute out of the column before ions that are derived from such important components are subjected to a $MS^2$ analysis. In other words, a risk arises of failing to perform a $MS^2$ analysis on the important components. To avoid this, it has been possible in the prior art to set as one condition for the selection of a precursor ion an upper limit to the number of times that ions with the identical mass/charge ratio (in actual practice, the mass/charge ratio that is deemed to be identical within the tolerated mass difference range) can be selected as a precursor ion.

However, with previous apparatuses, if a compound included an element such as bromine whose abundance ratio of stable isotopes is approximately 1:1, a possibility arises that after selecting ions that are derived from that compound as a precursor ion a predetermined number of times, ions that are derived from the same compound that include isotopes may continue to be selected as the precursor ion. The result would be for a $MS^2$ analysis to not be performed on other compounds or, even if the $MS^2$ analysis is performed, for the $MS^2$ spectrum that is generated to not have sufficient sensitivity due to the drop in the concentration of that component.

PRIOR ART LITERATURE

Patent Literature

Patent Literature 1: JP 2008-298427 A
Patent Literature 2: International Publication 2009/095957 Pamphlet Non-Patent Literature Non-Patent Literature 1: "Liquid Chromatograph Mass Spectrometer LCMS-IT-TOF Automatic $MS^n$ Function," (online), Shimadzu Corporation, (search performed on May 25, 2010), Internet (URL: http://www.an.shimadzu.co.jp/lcms/it-tof10.htm)

OVERVIEW OF THE INVENTION

Problems to be Solved by the Invention

The present invention has been made in light of the afore-described problems, and in a chromatogram-mass spectrometer wherein $MS^2$ analysis is performed by automatically selecting an appropriate precursor ion based on the results of an MS analysis that is not accompanied by a dissociation operation such as a CID, it is the object of the present invention to provide a chromatograph-mass spectrometer wherein good $MS^2$ analysis results can be obtained for a wide variety of components by avoiding the situation where ions derived from substantially identical components are repeatedly selected many times as the precursor ions.

Means for Solving the Problems

In a chromatograph-mass spectrometer that combines a chromatography unit for separating in a time direction the specimen components that are included in a specimen and a mass spectrometry unit that is capable of selectably performing a $MS^2$ analysis that is either accompanied by or not accompanied by a dissociation operation on the ions that are derived from the specimen components, the present invention which was made for solving the afore-described problems is a chromatograph-mass spectrometer comprising:

a) a selection condition setting means for allowing a user to enter the selection condition to be used for selecting a precursor ion for $MS^2$ analysis based on a MS spectrum that is obtained by MS analysis, one such selection condition that can be entered being information that defines a difference in mass/charge ratio from the mass/charge ratio of a precursor ion used in a $MS^2$ analysis that is executed so that a mass/charge ratio range to be used for excluding for selection as a precursor ion can be set after a $MS^2$ analysis is performed on a precursor ion;

b) an analysis control means for controlling said mass spectrometry unit so that MS analysis for obtaining an MS spectrum and $MS^2$ analysis performed on a precursor ion identified by a precursor selection means further described below are repeatedly executed; and c) a precursor selection means for extracting a precursor ion according to a selection condition that is set by said selection condition setting means for the MS spectrum that was obtained by a MS analysis and instructing said analysis control means wherein, after a $MS^2$ analysis is repeated a predetermined number of times using as a precursor ion an ion that meets the selection condition, a mass/charge ratio range that is determined by the mass/charge ratio difference that is set by said selection condition setting means with respect to the mass/charge ratio of the precursor ion is excluded from selection as a precursor ion for a predetermined time period.

With the chromatograph-mass spectrometer according to the present invention, it is good if the user can use the selection condition setting means to set, as one of the selection conditions, the "predetermined count" that defines the number of times that the $MS^2$ analysis will be repeated while selecting the ions that meet the selection condition for use as the precursor ions. Similarly with respect to the "predetermined time" to be used for excluding an excluded mass/charge ratio range in the selection of a precursor ion, it is good if the user can use the selection condition setting means to set, as one of the selection conditions, the "predetermined time" during which a mass/charge ratio range will be excluded in the selection of a precursor ion.

Furthermore, as a basic condition in selecting a precursor ion for $MS^2$ analysis based on a MS spectrum, it is good, for example, to select from among the peaks in the $MS^2$ spectrum, the peak with the highest strength signal that still exceeds the lower limit value. If a selection condition such as this is set, the precursor selection means follows the afore-described selection condition and, if the mass/charge ratio of a peak that is selected as a precursor ion candidate belongs within the afore-described excluded mass/charge ratio range, this candidate is excluded, and the peak with the next highest signal strength is selected.

With a chromatograph-mass spectrometer according to the present invention, the value of the mass/charge ratio difference (lower limit value) which defines the excluded mass/charge ratio range is set so that the mass difference of typical stable isotopes is covered. This means that it is good to set the mass/charge ratio difference to, for example, a value of 2 or more.

With a chromatograph-mass spectrometer according to the present invention, while an analysis is being executed, the precursor selection means uses a selection condition such as the afore-described that was set by the selection condition setting means on an actual MS spectrum that was obtained by a MS analysis to select a precursor ion. The analysis control means is instructed of the precursor ion so that a $MS^2$ analysis using as the precursor ion the ion that meets the selection condition is repeated a predetermined number of times. After the $MS^2$ analysis on a certain precursor ion is repeated a predetermined number of times, the precursor selection means excludes from possible selection as a precursor ion for a predetermined length of time those ions whose mass/charge ratio falls within the excluded mass/charge ratio range which is determined by the selection condition setting means based on the mass/charge ratio difference with respect to the mass/charge ratio of the precursor ion. This means that ions that are derived from a component that is substantially identical to the component from which the precursor ion that was subjected to the $MS^2$ analysis was derived from but whose mass is slightly different because it is a different isotope is not selected as a precursor ion.

Furthermore, by setting the value of the mass/charge ratio difference (lower limit value)—which is a value that can be set by the user—to be larger than the value that is sufficient for covering the mass difference of common stable isotopes, it is possible to include among the excluded ions not just ions that are derived from components that include isotopes but also adduct ions that are added with a specific substance (such as sodium and ammonium) during ionization. Since these adduct ions are substantially identical to ions without the specific adducts, excluding these ions from possible selection as a precursor ion increases the chance for ions derived from a different component to be selected as a precursor ion.

As for the difference in the mass/charge ratio that is used for defining the excluded mass/charge ratio range, it is preferable if the difference values can be independently defined in the direction of larger mass/charge ratio value and in the direction of smaller mass/charge ratio value.

Effects of the Invention

With a chromatograph-mass spectrometer according to the present invention, once an ion that is derived from a certain compound is automatically selected as a precursor ion and a $MS^2$ analysis is executed once or repeated more times, the selection as a precursor ion of an ion derived from a substantially identical compound that includes a stable isotope whose mass is different is avoided. This means that even if a plurality of compounds were to elute out almost simultaneously from a chromatograph column, the use of only the same compound in the $MS^2$ analyses is prevented, increasing the probability that $MS^2$ analysis results will be obtained for a wide variety of compounds. As a result, when analyzing a specimen that includes a wide variety of compounds, the possibility of a compound being overlooked and not being subjected to $MS^2$ analysis is reduced.

BRIEF DESCRIPTION OF THE FIGURES

FIG. 2 shows one example of a precursor selection condition setting screen in the present embodiment as a LC-MS system.

EMBODIMENTS OF THE INVENTION

Figure 1:
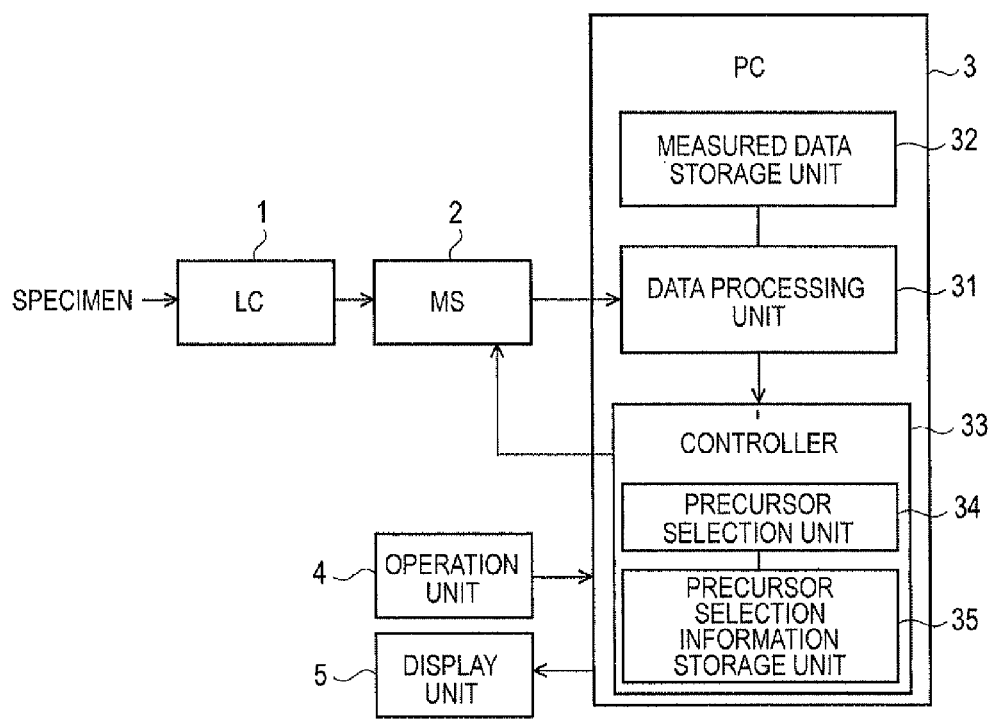
FIG. 1 shows a schematic view of the configuration of one embodiment of a LC-MS system according to the present invention.

One embodiment of a chromatograph-mass spectrometer according to the present invention as a LC-MS system is described next with reference to figures. FIG. 1 shows a schematic view of an embodiment of the present invention as a LC-MS system.

The system includes: a liquid chromatograph (LC) 1 which separates by time the components that are included in a liquid specimen; a mass spectrometer (MS) 2 which detects and separates the separated components according to mass/charge ratio m/z and which is capable of performing a $MS^2$ analysis; and a personal computer (PC) 3 which processes the data obtained by the mass spectrometer 2 and controls the operation of the mass spectrometer 2. A dedicated data processing/control software is installed in the personal computer 3. By executing the software on the personal computer 3, the functions of the controller 33 and the illustrated data processing unit 31, measured data storage unit 32, precursor selection unit 34, precursor selection information storage unit 35 and the like are realized. A display unit 5 and an operation unit 4 such as a keyboard or a pointing device such as a mouse are connected to the personal computer 3.

The mass spectrometer 2 is a triple quadrupole mass spectrometer wherein the precursor ion that is selected by a quadrupole mass filter in a preceding stage is dissociated by CID in a collision chamber and the product ions that are generated are separated and detected according to mass by a quadrupole mass filter in a later stage. However, so long as it is capable of performing an MS analysis and a $MS^2$ analysis, the specific configuration of the mass spectrometer 2 does not matter. It may be, for example, an ion trap mass spectrometer wherein ions that are derived from a specimen are trapped by an ion trap and the subsequent selection of a precursor ion, CID and separation of the product ions by mass are performed inside the ion trap, or may be an ion trap time-of-flight mass spectrometer wherein ions that are derived from a specimen are trapped by an ion trap and the subsequent selection of a precursor ion and CID are performed in the ion trap but the separation of the product ions by mass are performed inside a time-of-flight mass spectrometer that is situated outside the ion trap.

With the LC-MS system according to the present embodiment, a person performing the analysis (user) performs a predetermined operation on the operation unit 4 before the analysis is performed and sets the precursor ion selection conditions to be used for the automatic selection of a precursor ion. The information that is entered and set here is stored in a precursor selection information storage unit 35 and is referenced when an automatic $MS^2$ analysis further described below is performed. FIG. 2 shows one example of a precursor selection condition setting screen.

In FIG. 2, "signal strength lower limit value" is a parameter that defines the lower limit value of the signal strength in a MS spectrum to be used for selecting a precursor ion. Here, among the peaks that appear in a MS spectrum, the peak appearing in the MS spectrum with the highest signal strength and exceeding the lower limit value is selected. The "minimum repeating count" parameter defines the number of times that a $MS^2$ analysis will be repeated on the same precursor ion when performing an $MS^2$ analysis by selecting an ion as a precursor ion. If a check mark is placed in the "automatic exclusion" checkbox, the precursor ion automatic exclusion function becomes effective. In that case, the "automatic exclusion period" parameter defines the time during which automatic exclusion will be effective. The "excluded m/z range" parameter defines the mass/charge ratio difference to be used for automatic exclusion in relationship to the mass/charge ratio of the precursor ion that was automatically excluded. In the example shown in FIG. 2, assuming that the mass/charge ratio of the precursor ion that was automatically excluded is M, the range of the mass/charge ratio that will be automatically excluded is M−10 through M+25. The automatic exclusion period is for 600 seconds starting from when the $MS^2$ analysis on the precursor ion with a mass/charge ratio for automatic exclusion was repeated a minimum repeating count of "5" times.

The precursor selection conditions can be more elaborately set. For example, ions with a specific mass/charge ratio may be registered in an excluded ions list or a preferential ions list so that ions that are registered in the excluded ions list are excluded from selection as a precursor ion no matter how strong the signal strength may be, and ions that are registered in the preferential ions list are preferentially selected as a precursor ion no matter how weak the signal strength may be as long as there is a peak. Also, instead of starting the sequential selection of precursor ion candidates with ions with the highest signal strength, it is also acceptable to select as precursor ion candidates the ions whose mass/charge ratio is either the smallest or the largest so long as the signal strength exceeds the lower limit value.

Figure 3:
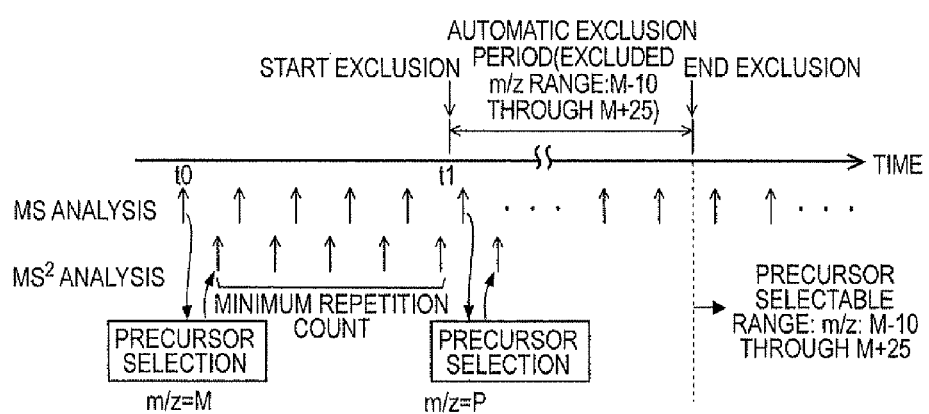
FIG. 3 is a timing chart showing the operation of an automatic $MS^2$ analysis in the present embodiment as a LC-MS system.
Figure 4:
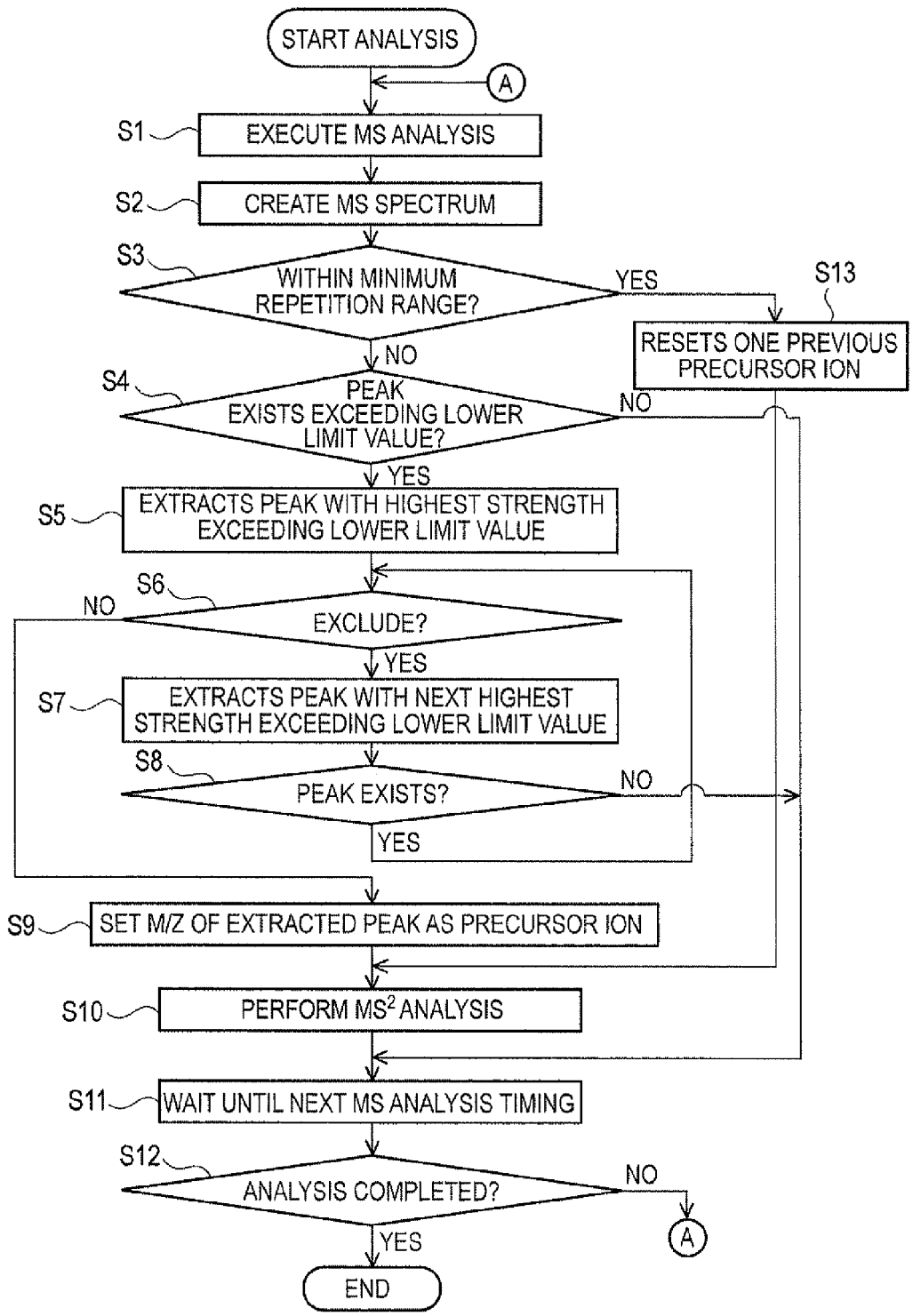
FIG. 4 is a flowchart showing the controls and processes that are executed during the execution of an automatic $MS^2$ analysis in the present embodiment as a LC-MS system.

One example of the execution of an automatic $MS^2$ analysis in an embodiment of the present invention as a LC-MS system is described next with reference to the timing chart shown in FIG. 3 and the flowchart shown in FIG. 4.

When an instruction to start analysis is issued, the analysis is started and a liquid specimen is introduced to the liquid chromatograph 1. As the components that are included in the specimen pass through a column (not illustrated), the components are separated by time as they elute out of the column. In accordance with the control implemented by the controller 33, the mass spectrometer 2 repeats the scanning and measurement (MS analysis) using a certain time interval accompanied by a mass scanning over a predetermined mass/charge ratio range. When one MS analysis is completed by the mass spectrometer 2 (step S1), data constituting one MS spectrum identified as, for example, A or C in FIG. 5 is obtained. The data processing unit 31 prepares a MS spectrum based on the data that is obtained (step S2).

The precursor selection unit 34 in the controller 33 first decides (step 3) whether or not the MS spectrum is still within the minimum repeating range that is decided by the afore-described "minimum repeating count." If it is still within the minimum repeating range, a new precursor ion selection process is not performed, and the precursor ion that was used in the immediately previous $MS^2$ analysis that was performed is reset (step S13), and the process proceeds to step S10. On the other hand, if the MS spectrum is not within the minimum repeating range, the process jumps from step S3 to step S4 and subsequent where the automatic precursor ion selection process is performed. In other words, a determination is made (step S4) as to whether or not, in the MS spectrum that was obtained, there is a peak whose signal strength exceeds the lower limit value that was entered as one of the precursor selection conditions. If not even one peak in the MS spectrum that was obtained has a signal strength that is equal to or greater than the lower limit value, this means that there is noprecursor ion to be selected, and the process proceeds from step S4 to S11. In this case, no $MS^2$ analysis is performed, and the next MS analysis timing is awaited.

If a determination is made in step S4 that there is at least one peak whose signal strength is equal to or greater than the lower limit value, the precursor selection unit 34 selects the peak with the highest strength (step S5). Then, a decision is made in step S6 as to whether or not the mass/charge ratio of the peak that was extracted falls within the mass/charge ratio range that is determined by the mass/charge ratio M of the precursor ion of the $MS^2$ analysis that was performed immediately before and the aforesaid "excluded m/z range" and whether or not the requirement on the exclusion period that is determined by the aforesaid "automatic exclusion period" is met, that is, a determination is made as to whether or not the peak should be excluded from selection as a precursor. For example, if the selection condition is set as shown in FIG. 2, peaks whose mass/charge ratio falls within the mass/charge ratio range of M−10 through M+25 are excluded from possible selection as a precursor.

If the peak that is extracted in step S5 is one that should be excluded from possible selection as a precursor, the precursor selection unit 34 extracts the peak with the next strongest signal strength from among the peaks whose signal strength is equal to or greater than the lower limit value (step S7). If a peak is extracted in this step, the result of the decision in step S8 becomes "Yes" and the process returns to step S6. If a peak is not extracted, the process moves from step S8 to step S11 where the process waits for the next MS analysis timing. Hence, with the processes performed in steps S5 through S8, peaks are sequentially extracted in the direction of lower signal strength until a peak that should not be excluded for selection as a precursor and whose signal strength is equal to or exceeds the lower limit value is determined. If a peak that should not be excluded for selection as a precursor is found in a MS spectrum, the process proceeds from step S6 to step S9 where the mass/charge ratio of the peak that was extracted is set as the precursor ion for the next $MS^2$ analysis. In step S10, controller 33 controls the operation of the mass spectrometer 2 so that a $MS^2$ analysis is performed on the precursor ion that was set in step S9 or S13 following a MS analysis that was performed in step S1.

Figures 5A, 5B:
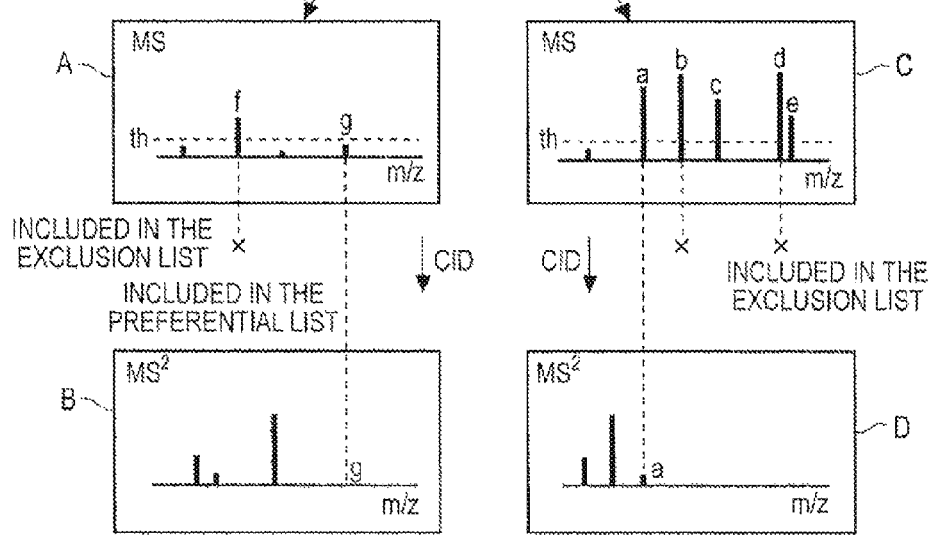
FIG. 5 shows a schematic view of the operation of the automatic $MS^2$ analysis in a previous chromatograph-mass spectrometer.

The data processing unit 31 obtains a $MS^2$ spectrum data in connection with the $MS^2$ analysis and stores the $MS^2$ spectrum data in the measured data storage unit 32. Once the $MS^2$ analysis is completed, the timing for performing the next MS analysis is awaited (step S11). If the analysis termination timing that is decided in advance has not arrived, the process returns from step S12 to S1. As shown in FIG. 3, the MS analysis is repeated using a predetermined time interval, and a MS spectrum is obtained from each MS analysis. FIG. 5(a) shows a TIC which is obtained by adding all of the ion strengths that are included in one MS spectrum and arranging them in the time direction.

An $MS^2$ analysis is performed following a MS analysis unless a precursor ion could not be extracted from the results of the MS analysis. As FIG. 3 shows, if the afore-described processes that are performed in steps S4 through S8 on the MS spectrum that was obtained at time t0 result in the extraction of a suitable precursor ion (m/z=M) and a $MS^2$ analysis is performed, the $MS^2$ analysis is unconditionally repeated (meaning that even if the signal strength of the ion were to go to zero) on the same precursor ion for the number of times, "5," that is defined as the "minimum repeating count." During the 600-second automatic exclusion period that starts from time t1 when the repeated execution of $MS^2$ analysis is completed, the mass/charge ratio range of M−10 to M+25 is excluded from possible selection as a precursor. To explain, during the automatic exclusion period, even if in the MS spectrum a peak with a strong signal strength were to be present in the mass/charge ratio range of M−10 to M+25, the peak is not selected as the precursor ion. This increases the possibility that an ion with a mass/charge ratio other than between M−10 and M+25 is selected as a precursor ion.

For example, if the original component from which the precursor ion was selected based on the MS spectrum that was obtained at time t0 includes elements (such as bromine and chlorine) whose abundance ratio of stable isotopes is relatively close, it is expected that peaks derived from substantially identical components that include such isotopes will appear at different mass/charge ratio positions in the MS spectrum. In that case, if after repeating the MS² analysis on the same precursor ion by the number of times specified by the minimum repeating count, even if the strength of the component that includes the isotopes is sufficiently high in the MS spectrum, because the mass/charge ratio falls within the range of M−10 to M+25, the possibility of selecting as precursor ion the ions that are derived from the same component that includes isotopes is eliminated. This also prevents ions that are derived from the same component that includes isotopes from being selected as a precursor ion in excess of the minimum repeating count, allowing an MS² analysis to be performed on ions derived from a different component.

The primary target of the afore-described automatic exclusion from precursor selection is the ions derived from components that include isotopes. However, by setting the upper value (increasing value direction) of the excluded m/z range to a value of 23 or more, it is possible to exclude from possible selection as a precursor not just components that include isotopes of different mass but also sodium adduct ions and ammonium adduct ions that are derived from the target component. Such adduct ions can be excluded because they are, in terms of MS² analysis, no different from the original ions. Excluding the adduct ions from possible selection as a precursor increases the possibility that MS² analysis is performed on ions derived from a different component and reduces the possibility that MS² analysis goes unperformed.

The afore-described embodiment entails the use of the present invention in a LC-MS, but it should be obvious that the present invention can also be used in a GC-MS. Furthermore, the afore-described embodiment is only one example of the present invention, and it should be obvious that various modifications, corrections and additions can be made without deviating from the gist of the present invention and the claims of the present application.

DESCRIPTION OF THE NUMERICAL REFERENCES

1. Liquid chromatograph (LC)
2. Mass spectrometer (MS)
3. Personal computer (PC)
31. Data processing unit
32. Measured data storage unit
33. Controller
34. Precursor selection unit
35. Precursor selection information storage unit
4. Operation unit
5. Display unit

What is claimed is:

1. A chromatograph-mass spectrometer system comprising:
  a chromatography unit for separating components included in a specimen by time;
  a mass spectrometry unit for performing an MS² analysis that is accompanied by or not accompanied by a dissociation operation on the ions from the components;
  a computer readable medium containing software instructions, wherein execution of the software instructions by one or more processors of a computer system causes the processors to carry out the steps of:
  allowing a user to enter one or more selection conditions for selecting a precursor ion for MS² analysis based on an MS spectrum obtained by MS analysis, including a first selection condition for setting a minimum repetition count for executing the MS² analysis, a second selection condition for setting a mass/charge ratio range that is defined by a difference in mass/charge ratio from the mass/charge ratio of a precursor ion used in an MS² analysis and a third selection condition for setting an automatic exclusion period;
  controlling said mass spectrometry unit for executing MS analysis for obtaining an MS spectrum followed by MS² analysis performed on a precursor ion and repeating the MS and MS² analyses in that order on the same precursor ion under the first condition;
  selecting a precursor ion according to the selection conditions for an MS spectrum obtained from an MS analysis, wherein after the minimum repetition count is satisfied under the first selection condition, the second selection condition is used to select from the MS spectrum, a precursor ion outside the mass/charge ratio range; and
  after repeating the MS analysis and the MS² analysis in that order a predetermined number of times on the selected precursor ion that meets the first selection condition in the step of controlling said mass spectrometry unit, excluding an ion as a precursor ion that falls within the mass/charge ratio range, which is determined by the mass/charge ratio difference with respect to the mass/charge ratio of the selected precursor ion, for the automatic exclusion period while repeating the MS analysis, and after the automatic exclusion period, the precursor ion becomes selectable within the mass/charge ratio range.

2. A chromatograph-mass spectrometer system according to claim 1, wherein the mass/charge ratio difference is set to be larger than a mass/charge ratio difference of a stable isotope of the selected precursor ion and the selected precursor ion.

3. A chromatograph-mass spectrometer system according to claim 1, wherein the mass/charge ratio difference is set to be 23 m/z or more.

4. A chromatograph-mass spectrometer system according to claim 1, wherein the mass/charge ratio difference is set to a mass charge ratio difference of the selected precursor ion with an adduct ion and the selected precursor ion without the adduct ion.

5. A chromatograph-mass spectrometer system according to claim 4, wherein the adduct ion is a sodium adduct ion or an ammonium adduct ion.

6. A method for executing a chromatograph-mass spectrometer system, said method comprising:
  allowing a user to enter one or more selection conditions for selecting a precursor ion for MS² analysis based on an MS spectrum obtained by MS analysis, including a first selection condition for setting a minimum repetition count for executing the MS² analysis, a second selection condition for setting a mass/charge ratio range that is defined by a difference in mass/charge ratio from the mass/charge ratio of a precursor ion used in an MS² analysis and a third selection condition for setting an automatic exclusion period;
  controlling said mass spectrometry unit for executing MS analysis for obtaining an MS spectrum followed by MS² analysis performed on a precursor ion and repeating the MS and MS² analyses in that order on the same precursor ion under the first condition;
  selecting a precursor ion according to the selection condition for an MS spectrum obtained from an MS analysis, wherein after the minimum repetition count is satisfied under the first selection condition, the second selection condition is used to select from the MS spectrum, a precursor ion outside the mass/charge ratio range; and after repeating the MS analysis and the $MS^2$ analysis in that order a predetermined number of times on the selected precursor ion that meets the first selection condition in the step of controlling said mass spectroscopy unit, excluding an ion as a precursor ion that falls within the mass/charge ratio range, which is determined by the mass/charge ratio difference with respect to the mass/charge ratio of the selected precursor ion, for the automatic exclusion period while repeating the MS analysis, and after the automatic exclusion period, the precursor ion becomes selectable within the mass/charge ratio range.

7. A method for executing a chromatograph-mass spectrometer system according to claim 6, wherein the mass/charge ratio difference is set to be larger than a mass charge ratio difference of a stable isotope of the selected precursor ion and the selected precursor ion.

8. A method for executing a chromatograph-mass spectrometer system according to claim 6, wherein the mass/charge ratio difference is set to be 23 m/z or more.

9. A method for executing a chromatograph-mass spectrometer system according to claim 6, wherein the mass/charge ratio difference is set to a mass charge ratio difference of the selected precursor ion with an adduct ion and the selected precursor ion without the adduct ion.

10. A method for executing a chromatograph-mass spectrometer system according to claim 9, wherein the adduct ion is a sodium adduct ion or an ammonium adduct ion.

* * * * *